United States Patent [19]

Satake et al.

[11] Patent Number: 5,569,662
[45] Date of Patent: Oct. 29, 1996

[54] QUINUCLIDINE DERIVATIVES AS SUBSTANCE P ANTAGONISTS

[75] Inventors: Kunio Satake, Handa; Hiroaki Wakabayashi, Kariya; Masami Nakane, Aichi, all of Japan

[73] Assignee: Pfizer Inc., New York, N.Y.

[21] Appl. No.: 313,289
[22] PCT Filed: Mar. 5, 1993
[86] PCT No.: PCT/US93/01810
   § 371 Date: Oct. 3, 1994
   § 102(e) Date: Oct. 3, 1994
[87] PCT Pub. No.: WO93/19064
   PCT Pub. Date: Sep. 30, 1993

[30] Foreign Application Priority Data

Mar. 23, 1992 [JP] Japan ................................. 4-065337

[51] Int. Cl.$^6$ .......................... C07D 453/02; A61K 31/445
[52] U.S. Cl. ............................................. 514/305; 546/133
[58] Field of Search .............................. 546/133; 514/305

[56] References Cited

PUBLICATIONS

CA 119: 95339 (JP 91–146826) 910522 (1991).

*Primary Examiner*—Richard D. Lovering
*Assistant Examiner*—Catherine Kilby Scalzo

*Attorney, Agent, or Firm*—Peter C. Richardson; Paul H. Ginsburg; Garth Butterfield

[57] ABSTRACT

Compounds useful in the treatment of inflammatory disorders, central nervous system disorders and other disorders of formula (I) and the pharmaceutically-acceptable salts thereof, wherein $X^1$ is alkoxy or halosubstituted alkoxy; $X^2$ is hydrogen, halogen, alkyl, alkenyl, alkynyl, alkoxy, alkylthio, alkylsulfinyl, alkylsulfonyl, halosubstitued alkyl, halosubstituted alkoxy, alkylamino, dialkylamino, alkylsulfonylamino (which may be substituted), N-alkyl-N-alkylsulfonylamino (which may be substituted), alkanoylamino (which may be substituted) or N-alkyl-N-alkanoylamino (which may be substituted); $Ar^1$ and $Ar^2$ are each, independently, thienyl, phenyl, fluorophenyl, chlorophenyl or bromophenyl; A is Y—$(CH_2)_m$—$CH(R^2)$—$(CH_2)_n$—$NR^1$—; $R^1$ is hydrogen, alkyl, benzyl or —$(CH_2)_p$—Y; $R^2$ is hydrogen, alkyl (which may be substituted), benzyl, 4-hydroxybenzyl, 3-indolylmethyl or —$(CH_2)_p$—Y; Y is —CN, —$CH_2Z$ or —COZ; Z is hydroxy, amino, alkoxy, alkylamino or dialkylamino; m, n and p are each, independently, 0, 1, 2 or 3; and $R^1$ and $R^2$ may be connected to form a ring.

14 Claims, No Drawings

QUINUCLIDINE DERIVATIVES AS SUBSTANCE P ANTAGONISTS

TECHNICAL FIELD

This invention relates to novel and useful peptidic quinuclidine derivatives of interest to those in the field of medical chemistry and chemotherapy. More particularly, it is concerned with a novel series of peptidic substituted 3-aminoquinuclidine, including their pharmaceutically acceptable salts and pharmaceutical compositions comprising such compounds, which are of special value in view of their ability to antagonize substance P. In this way, these compounds are of use in treating gastrointestinal disorders, central nervous system disorders, inflammatory diseases, asthma and pain or migraine.

BACKGROUND ART

E. J. Warawa in U.S. Pat. No. 3,560,510 discloses certain 3-amino-2-benzhydryl-quinuclidines as being useful as diuretic agents, with the corresponding unsubstituted 3-benzylamino compounds acting as intermediates for same. Additionally, E. J. Warawa et al. in the *Journal of Medicinal Chemistry*, Vol. 18, p. 587 (1975) extends this work to other members of the series wherein the 3-amino moiety is either ethylamino, β-phenylethyl amino, β-isopropylamino, or 2-furfurylamino, but in no instance is there any substitution on the phenyl group itself and the 2-benzhydryl moiety is always symmetrically substituted (or unsubstituted).

Furthermore, neither of the aforementioned documents teaches or suggests any of these compounds to be useful as substance P antagonists.

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, Vol. 25, p. 1009 (1982)), as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc (see D. Regoli in *"Trends in Cluster Headache"* edited by F. Sicuteri et al., Elsevier Scientific Publishers, Amsterdam, 1987, pp. 85–95).

In the recent past, some attempts have been made to provide peptide-like substances that are antagonists for substance P and other tachykinin peptides in order to more effectively treat the various disorders and diseases listed above. The peptide-like nature of such substances make them too labile from a metabolic point of view to serve as practical therapeutic agents in the treatment of disease. The non-peptidic antagonists of the present invention, on the other hand, do not possess this drawback, being far more stable from a metabolic point of view than the previously-discussed prior art agents.

Among documents of interest regarding the present invention, there are WO 90/05729 (corresponding to U.S. Pat. No. 5,162,339), JP (appln.) 325237/91 (corresponding to PCT Patent Publication No. WO 92/20676) and JP (appln.) 065337/92. (All documents cited herein, including the foregoing, are incorporated herein by reference in their entireties for all purposes.)

Particularly, WO 90/05729 discloses a series of cis-3-[(cyclic)methylamino]-2-[(α-substituted)arylmethyl]quinuclidines including 2-benzhydryl derivatives, 2-substituted benzhydryl derivatives (wherein the substituents were alkyl, alkoxy, halogen and the like), 2-(bis-(2-thienyl)methyl) derivatives and the like.

JP (appln.) 325237/91 discloses mainly a series of 3-[2-methoxy-5-(substituted)benzylamino]-2-benzhydryl quinuclidines including 4-alkenyl derivatives, 6-phenethyl derivatives, 5- and 6-dialkylaminocarbonyl derivatives, 5-dialkylaminoalkyl derivatives, 6-hydroxyalkyl derivatives, 5-alkylaminocarbonyl derivatives, 5-aminocarbonyl derivatives, 5-carboxyl derivatives, 5- and 6-alkoxycarbonyl derivatives, 5-(N-alkoxy-N-alkyl)aminocarbonyl derivatives, 5-morpholinocarbonyl derivatives and the like.

Additionally, the quinuclidine compounds disclosed in JP (appln.) 325237/91 have various kinds of substituents also at the 5-position on the benzylamino moiety, i.e. alkoxy (methoxy), alkyl (isopropyl), alkylthio (methylthio), halosubstituted alkoxy (trifluoromethoxy), halogen, alkylsulfinyl (methylsulfinyl), dialkylamino (dimethylamino) and the like.

Furthermore, it shows that compounds disclosed in both WO 90/05729 and JP (appln.) 325237/91 have substance P antagonist activity, anti-inflammatory activity and anti-psychotic activity.

Under the circumstances, the present inventors have worked to prepare compounds useful as substance P antagonists, and after extensive research, have succeeded in synthesizing a series of compounds as will be disclosed in detail herein.

BRIEF DISCLOSURE OF THE INVENTION

The present invention provides novel peptidic 3-aminoquinuclidine derivatives of the following chemical formula

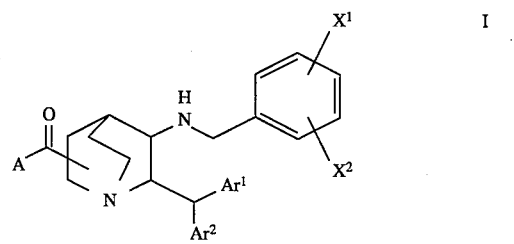

and the pharmaceutically-acceptable salts thereof, wherein $X^1$ is $C_1$–$C_5$ alkoxy or halosubstituted ($C_1$–$C_5$) alkoxy;

$X^2$ is hydrogen, halogen, $C_1$–$C_5$ alkyl, $C_2$–$C_5$ alkenyl, $C_2$–$C_5$ alkynyl, $C_1$–$C_5$ alkoxy, $C_1$–$C_5$ alkylthio, $C_1$–$C_5$ alkylsulfinyl, $C_1$–$C_5$ alkylsulfonyl, halosubstituted ($C_1$–$C_5$) alkyl, halosubstituted ($C_1$–$C_5$) alkoxy, $C_1$–$C_5$ alkylamino, dialkylamino having from 1 to 5 carbon atoms in each alkyl moiety, $C_1$–$C_5$ alkylsulfonylamino (which may be substituted by halogen), N-($C_1$–$C_5$)alkyl-N-($C_1$–$C_5$)alkylsulfonylamino (which may be substituted by halogen in the alkylsulfonyl moiety), $C_1$–$C_5$ alkanoylamino (which may be substituted by halogen) or N-($C_1$–$C_5$)alkyl-N-

($C_1$–$C_5$)alkanoylamino (which may be substituted by halogen in the alkanoyl moiety);

$Ar^1$ and $Ar^2$ are each, independently, thienyl, phenyl, fluorophenyl, chlorophenyl or bromophenyl;

A is Y—$(CH_2)_m$—$CH(R^2)$—$(CH_2)_n$—$NR^1$—;

$R^1$ is hydrogen, $C_1$–$C_5$ alkyl, benzyl or —$(CH_2)_p$—Y;

$R^2$ is hydrogen, $C_1$–$C_5$ alkyl (which may be substituted by a substituent selected from the group consisting of hydroxy, amino, methylthio and mercapto), benzyl, 4-hydroxybenzyl, 3-indolylmethyl or —$(CH_2)_p$—Y;

Y is —CN, —$CH_2Z$ or —COZ;

Z is hydroxy, amino, $C_1$–$C_5$ alkoxy, $C_1$–$C_5$ alkylamino or dialkylamino having from 1 to 5 carbon atoms in each alkyl moiety;

m, n and p are each, independently, 0, 1, 2 or 3; and $R^1$ and $R^2$ may be connected to form a ring.

The compounds of formula I are useful as substance P antagonists. Therefore the present invention also relates to a method of treating or preventing a condition selected from the group consisting of inflammatory diseases (e.g, arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic disease such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also includes pharmaceutical compositions for antagonizing mammal's Substance P which comprises a pharmaceutically acceptable carrier or diluent and a compound of formula I or a pharmaceutically acceptable salt thereof. These compositions are useful for treatment or prevention of a condition selected from the group consisting of inflammatory diseases (e.g, arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic disease such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human.

Preferred compounds of this invention are the following:

(3R,4S,5S ,6S)-N-carbamoylmethyl-5-(5-isopropyl-2-methoxybenzylamino)- 6-diphenylmethyl-1-azabicyclo[2.2.2]octane-3-carboxamide;

(3R,4S,5S,6S)-N-carboxymethyl-5-(5-isopropyl-2-methoxybenzylamino)-6-diphenylmethyl-1-azabicyclo[2.2.2]octane-3-carboxamide;

(3R,4S,5S ,6S)-3-(2-carbamoylpyrrolidin-1-yl)carbonyl-5-(5-isopropyl-2-methoxybenzylamino)-6-diphenylmethyl-1-azabicyclo[2.2.2]octane;

(3R*,4S*,5S*,6S*)-N-(1-carbamoylethyl)-5-(5-isopropyl-2-methoxybenzylamino)- 6-diphenylmethyl-1-azabicyclo[2.2.2]octane-3-carboxamide;

(3R,4S,5S,6S)-N-(1-carbamoyl-3-methylbutyl)-5-(5-isopropyl-2 -methoxy-benzylamino)-6-diphenylmethyl-1-azabicyclo[2.2.2]octane-3-carboxamide;

(3R,4S,5S,6S)-N-(2-carbamoylethyl)-5-(5-isopropyl-2-methoxybenzylamino)- 6-diphenylmethyl-1-azabicyclo[2.2.2]octane-3-carboxamide.

DETAILED DISCLOSURE OF THE INVENTION

In this specification:

the terms "halogen" or "halo" is used herein to mean radicals derived from the elements fluorine, chlorine, bromine and iodine;

the term "alkyl" is used herein to mean straight or branched hydrocarbon chain radicals including, but not limited to, methyl, ethyl, n-propyl, isopropyl, n-butyl, isobutyl, s-butyl, t-butyl, and the like;

the term "alkenyl" is used herein to mean straight or branched hydrocarbon chain radicals having one double bond including, but not limited to, ethenyl, 1- and 2-propenyl, 2-methyl-1-propenyl, 1- and 2-butenyl and the like;

the term "alkynyl" is used herein to mean straight or branched hydrocarbon chain radicals having one triple bond including, but not limited to, ethynyl, propynyl, butynyl and the like;

the term "alkoxy" is used herein to mean —$OR^3$ ($R^3$ is alkyl) including, but not limited to, methoxy, ethoxy, propoxy, isopropoxy, n-butoxy, isobutoxy, s-butoxy, t-butoxy and the like;

the term "alkylthio" is used herein to mean —$SR^4$ ($R^4$ is alkyl) including, but not limited to, methylthio, ethylthio, n-propylthio, isopropylthio, n-butylthio, isobutylthio, s-butylthio, t-butylthio and the like;

the term "alkylsulfinyl" is used herein to mean —$SOR^5$ ($R^5$ is alkyl) including, but not limited to, methylsulfinyl, ethylsulfinyl, propylsulfinyl, n-butylsulfinyl, isobutylsulfinyl, s-butylsulfinyl, t-butylsulfinyl and the like;

the term "alkylsulfonyl" is used herein to mean —$SO_2R^6$ ($R^6$ is alkyl) including, but not limited to, methylsulfonyl, ethylsulfonyl, propylsulfonyl, n-butylsulfonyl, isobutylsulfonyl, s-butylsulfonyl, t-butylsulfonyl and the like;

the term "alkylsulfonylamino (which may be substituted by halogen)" is used herein to mean —$NHSO_2R^7$ ($R^7$ is alkyl which may be substituted) including, but not limited to, methylsulfonylamino, ethylsulfonylamino, trifluoromethylsulfonylamino and the like;

the term "N-alkyl-N-alkylsulfonylamino (which may be substituted by halogen in the alkylsulfonyl moiety)" is used herein to mean —$N(R^8)SO_2R^9$ ($R^8$ is alkyl and $R^9$ is alkyl which may be substituted) including, but not limited to, N-methyl-N-methylsulfonylamino, N-ethyl-N-methylsulfonylamino, N-n-propyl-N-methylsulfonylamino, N-isopropyl-N-methylsulfonylamino, N-methyl-N-trifluoromethylsulfonylamino, N-ethyl-N-trifluoromethylsulfonylamino, N-n-propyl-N-trifluoromethylsulfonylamino, N-isopropyl-N-trifluoromethylsulfonylamino and the like;

the term "alkylamino" and "dialkylamino" is used herein to mean —N(R$^{10}$)R$^{11}$ (R$^{10}$ is hydrogen or alkyl and R$^{11}$ is alkyl) including, but not limited to, methylamino, ethylamino, n-propylamino, isopropylamino, n-butylamino, t-butylamino, dimethyl-amino, diethylamino, ethylmethylamino and the like;

the term "alkanoylamino (which may be substituted by halogen)" is used herein to mean —NHCOR$^{12}$ (R$^{12}$ is alkyl which may be substituted by halogen) including, but not limited to, formylamino, acetylamino, propionylamino, butyrylamino, isobutyrylamino, trifluoroacetylamino and the like;

the term "N-alkyl-N-alkanoylamino (which may be substituted by halogen in the alkanoyl moiety)" is used herein to mean —N(R$^{13}$)COR$^{14}$ (R$^{13}$ is alkyl and R$^{14}$ is alkyl which may be substituted by halogen) including, but not limited to, N-acetyl-N-methylamino, N-acetyl-N-ethylamino, N-acetyl-N-n-propylamino, N-acetyl-N-isopropylamino, N-trifluoroacetyl-N-methylamino, N-trifluoroacetyl-N-ethylamino, N-trifluoroacetyl-N-n-propylamino, N-trifluoroacetyl-N-isopropylamino and the like;

the term "halosubstituted alkyl" is used herein to mean an alkyl radical as described above substituted with one or more halogens including, but not limited to, chloromethyl, trifluoromethyl, 2,2,2-trichloroethyl and the like;

the term "halosubstituted alkoxy" is used herein to mean an alkoxy radical as described above substituted with one or more halogens including, but not limited to, chloromethoxy, trifluoromethoxy, 2,2,2-trichloroethoxy and the like.

The compounds of the above formula I form acid addition salts. The pharmaceutically acceptable acid addition salts are those formed from acids which form non-toxic acid addition salts.

The novel compounds of the present invention can be prepared as described in the following reaction schemes and discussions. Unless otherwise indicated, X$^1$, X$^2$, Ar$^1$ and Ar$^2$ in the following reaction schemes and discussion are defined as above. The symbol A means herein properly protected amino acid such as its carboxamide derivatives.

GENERAL SYNTHETIC SCHEME

Route 1

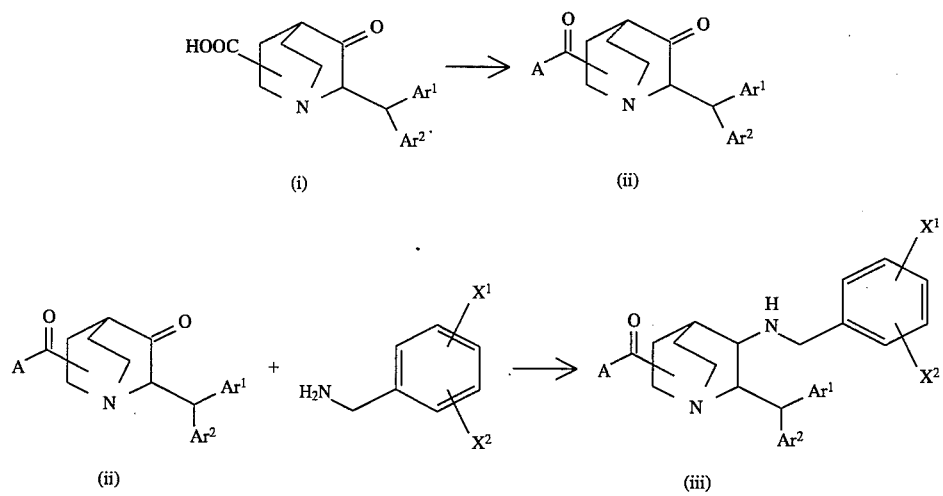

Route 2

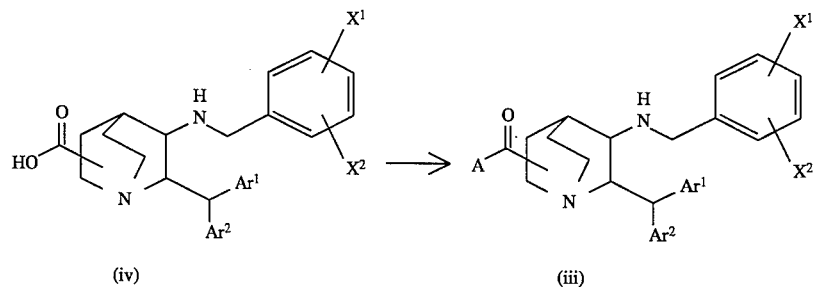

-continued
GENERAL SYNTHETIC SCHEME

Route 3

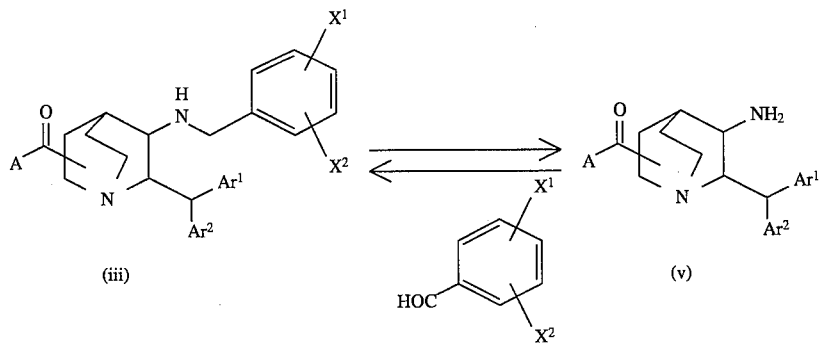

Starting compound (i) can be prepared from the corresponding carboxamide according to the procedure described in our prior application [JP(appln.) 325237/91] and following example 1.

Introduction of a protected amino acid into compound (i) to give compound (ii) can be carried out by a variety of conventional methods for peptide synthesis as described in *"Peptide synthesis, the basis and experiments"* edited by N. Izumiya, 1985 (Maruzen).

For instance, those methods include an activated ester method with acid chloride or mixed acid anhydride, and a condensation method employing an appropriate condensing agent which is selected from dicyclohexylcarbodiimide (DCC), watersolublecarbodiimide, 2-ethoxy-N-ethoxycarbonyl-1,2-dihydroquinoline, Bopagent, diethylcyanophosphonic acid and diphenylphospholylazide and the like.

If necessary, addition of tertiary amine such as triethylamine can promote the condensation reaction. Furthermore, in order to prevent racemization, employment of N-hydroxysuccinimide, N-hydroxybenzotriazole or 3,4-dihydro-3-hydroxy-4-oxo-1,2,3-benzotriazine etc. can bring a preferable result in this reaction.

Typically, compound (ii) can be prepared from compound (i) and an amino acid or its salt which is protected by amino group or mono- or dialkyl substituted amino group by the use of a peptide coupling reagent such as DCC or diethylcyanophosphonic acid in a reaction inert solvent such as methylene chloride, THF, DMF etc. in the presence of triethylamine.

Subsequently, resulting compound (ii) may be converted to compound (iii) by reductive amination. This route is relied on direct introduction of a corresponding benzylamino group at 3-position of the quinuclidine. This reaction is typically conducted by two steps.

In the first step, the imine formation from compound (ii) and a corresponding benzylamine is carried out by heating at its reflux temperature in a reaction inert solvent such as toluene or benzene etc. in the presence of catalytic amount of acid (e.g. p-toluenesulfonate or camphorsulfonic acid (CSA)) under a dehydrolytic condition.

Alternatively, Lewis acid such as aluminium chloride or titanium tetrachloride etc. can be used as the acid catalyst. Under such catalytic condition at from −78° C. to room temperature, employment of a solvent such as acetonitrile or methylene chloride and a dehydrating agent such as molecular sieves can bring a preferable result in this reaction.

In the second step, the imine is reduced to afford the claimed compound (iii). This reduction can be carried out by either catalytic hydrogenation, or reaction with suitable hydride reagents such as borohydrides, boranes or aluminum hydrides. Typically, $NaBH_4$, $NaBH_3CN$ or $NaBH(OAc)_3$ in the presence of acetic acid is used.

The above two reaction steps can be also carried out at one time continuously. At that time, employment of $NaBH_3CN$ in methanol in the presence of acetic acid is a effective procedure.

Finally, compound (iii) can be converted to the corresponding carboxylic acid [compound (iv)] by acidic hydrolysis in an inorganic acid such as HCl at room temperature to its reflux temperature for 30 minutes to several hours.

Furthermore, the resulting carboxylic acid (iv) can be converted to the corresponding ester by heating in an alcohol solvent in the presence of an acid catalyst.

Alternatively, compound (iii) can be also prepared according to the above synthetic route 2. Compound (iii) can be prepared by peptide condensation from compound (iv) as described in our own prior art [JP (appln.) 325237/1992] and an amino acid which may be protected at its carboxyl moiety. The generic synthetic condition for various peptide synthetic methods as described in synthetic route 1 can be used in this reaction. Under such a condition, employment a peptide coupling agent such as carbodiimide derivatives (ex. DCC etc.) in a solvent such as DMF or THF can bring a preferable result in the reaction of a protected amino acid (ex. carboxamide, lower alkyl ester or benzyl ester etc.) with compound (iv). At that time, optional addition of a base agent (ex. triethylamine etc.) can give a good result.

Furthermore, the method as described in the synthetic route 3 can be also used as the third method in order to prepare compound (iii) of the present invention. In this synthetic route, compound (iii) can be prepared by reductive amination of 3-amino quinuclidine (v) having a amino acid as a substituent A with a corresponding substituted benzaldehyde. This reductive amination reaction proceed easily under a standard reaction condition because it goes by way of a stable imine intermediate. Typically, employment of borane agent (e.g. $NaBH_3CN$ or $NaBH(Oac)_3$ etc.) gives a good result.

The starting compound (v) can be obtained by debenzylation of compound (iii). Preferable reaction condition for the debenzylation is hydrogenolysis with palladium catalyst (e.g., palladium or palladium hydroxide) which scarcely affects the other functional groups in the compound (v).

The objective compounds (iii) prepared by the above-mentioned methods can be isolated and purified by conventional procedures, such as recrystallization or chromatography.

As mentioned above, the synthetic methods include typically, but not limited to, the above three synthetic routes.

Inasmuch as the quinuclidine compounds of this invention all possess at least four asymmetric centers, they are capable of occurring in various stereoisomeric forms or configurations. Hence, the compounds can exist in separated (+)- and (−)-optically active forms, as well as in racemic or (±)-mixtures thereof. The present invention is meant to include all such forms within its scope. For instance, the diastereomers can be separated by methods well known to those skilled in the art, e.g., by fractional crystallization and the like, while the optically-active isomers can be obtained by resolving the final objective compounds or its intermediates with the standard procedure of organic chemistry.

Insofar as the majority of 3-benzylamino-2-benzhydryl quinuclidine compounds of this invention are basic compounds, they are all capable of forming a wide variety of different salts with various inorganic and organic acids.

Although the salts of the compounds of formula I must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter, subsequently convert the free base to a pharmaceutically acceptable acid addition salt, The acid addition salts of the quinuclidine base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methane sulfonate, benzenesulfonate, p-toluenesulfonate and pamoate [i.e., 1.1'-methylene-bis-(2-hydroxy-3-naphthoate)] salts.

Some quinuclidine compounds of the invention which have also acidic groups are capable of forming base salts with various pharmacologically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic quinuclidine derivatives. These particular non-toxic base salts include those derived form such pharmacologically acceptable cations as sodium, potassium, calcium and magnesium, etc. These salts can easily be prepared by treating the aforementioned acidic quinuclidine compounds with an aqueous solution containing the desired pharmacologically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active quinuclidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, and respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans.

Some compounds of the present invention, when tested as an antiinflammatory agent, exhibit a significant degree of activity in the mustard oil-induced rat foot edema test [described by F. Lembeck et al., *British Journal of pharmacology*, Vol. 105, p. 527 (1992)] and the capsaicin-induced plasma extravasation test in guinea pig ureter [described by A. Nagahisa et al., *European Journal of pharmacology*, Vol. 217, p. 191 (1992)].

The radiolabelled quinuclidine compounds of the above formula are useful as research and diagnostic tools in metabolism pharmacokinetic studies and in binding assays with the drug in both animal and human. Specific applications in research include radioligand binding assays, autoradiography studies and in vivo binding studies, while specific applications in the diagnostic area include studies of substance P receptor in the human brain, such as up/down regulation in a diseases state, and in vivo binding in the relevant tissues for inflammation, e.g., immune-type cell or cells that are directly involved in inflammatory bowel disorders and the like. Specifically, the radiolabelled forms of the quinuclidine compounds are the tritium and $^{-}$C-isotopes of substituted 3-aminoquinuclidine in this invention.

The active quinuclidine compounds hereinbefore described can be administered to a human subject via either the oral, parenteral or topical routes. In general, these compounds are most desirably administered in doses ranging from about 1.0 mg up to 200 mg per day, although variations will necessarily occur depending upon the weight and condition of the subject being treated and the particular route of administration chosen. However, a dosage level that is in the range of from about 0.05 mg to about 2 mg per kg of body weight per day is most desirably employed when using these compounds as antiinflammatory agents. Nevertheless, variations may still occur depending upon the individual response to said medicament, as well as on the type of pharmaceutical formulation chosen, the mode of administration and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules, preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH value is approximately eight) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in bovine caudate tissue or IM-9 cells employing radioactive ligands. The substance P antagonist activity of the herein described quinuclidine compounds is evaluated by the use of standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. In this test, some preferred compounds indicated low $IC_{50}$ values, in the range of 0.51–6.51 nM, with respect to inhibition of binding at its receptor. More preferable compounds indicated low $IC_{50}$ values of less than 0.1 nM.

The anti-inflammatory activity of the compounds of the present invention is demonstrated in the previously mentioned mustard oil-induced rat foot edema test.

In this test, anti-inflammatory activity is determined as the percent inhibition of plasma protein extravasation in the hind paw of female Sprague-Dawley rats (weighing 100–150 g) in response to the application of mustard oil to the dorsal skin.

The compounds of the present invention are dissolved in 0.1% methyl cellulose/water and dosed orally 1 hour before mustard oil challenge. After Evans Blue injection solution (50 mg/kg, dissolved in saline including 0.02% bovine serum albumin) is injected intravenously, rat's hind paw is painted with 5% mustard oil in paraffin oil and 20 minutes later the foot is amputated, frozen, pulverized and the Evans Blue dye is extracted and determined colorimetrically.

Alternatively, the antiinflammatory activity of the compounds of the present invention is demonstrated by a capsaicin-induced plasma extravasation test.

In this test, antiinflammatory activity is determined as the percent inhibition of plasma protein extravasation in the ureter of male Hartley guinea pigs (weighing 450–500 g) in response to the intraperitoneal injection of capsaicin into anesthetized animals.

The compounds of the present invention are dissolved in 0.1% methyl cellulose/water and dosed orally 1 hour before capsaicin challenge. Evans Blue dye (30 mg/kg) is administered intravenously 5 minutes before capsaicin challenge. The animals are killed 10 minutes after capsaicin injection and both right and left ureters are removed. The Evans Blue dye is extracted and determined colorimetrically.

In the above two tests, compounds are considered active if the difference in response between the drug-treated animals and a control group receiving the vehicle alone is statistically significant.

The anti-psychotic activity of the compounds of the present invention as neuroleptic agents for the control of various psychotic disorders is determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

The present invention is illustrated by the following examples. However, it should be understood that the invention is not limited to the specific details of these examples. Proton nuclear magnetic resonance spectra (NMR) were measured at 270 MHz, unless otherwise indicated, for solutions in deuterio trichloromethane ($CDCl_3$) and peak positions are expressed in parts per million (ppm) downfield from tetramethylsilane. The peak shapes are denoted as follows: s, singlet; d, doublet; t, triplet; m, multiplet; br, broad.

EXAMPLES

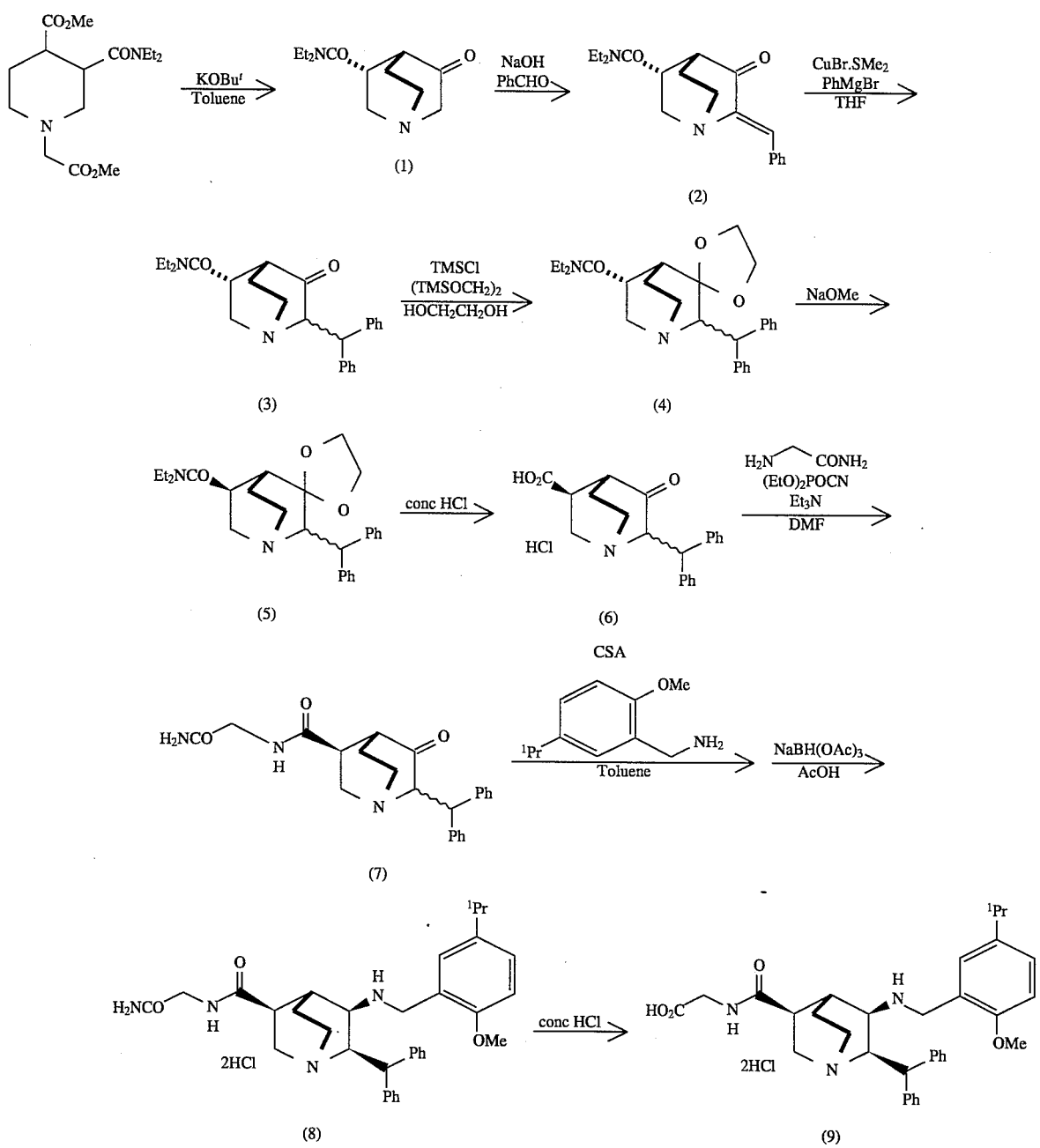

Example 1

(3R*,4S*,5S*,6S*)-N-Carbamoylmethyl-5-(5-isopropyl-2-methoxybenzylamino)-6-diphenylmethyl-1-azabicyclo.[2.2.2]octane-3-carboxamide dihydrochloride (A) (3R*,4R*)-N,N-Diethyl-5-oxo-1-azabicyclo[2.2.2]octane-3-carboxamide, 1

A solution of N,N-diethyl-4-methoxycarbonyl-1-(methoxycarbonyl)methyl piperidine-3-carboxamide (159 g, 0.503 mol) in toluene (700 ml) was added dropwise over a period 2.5 hours to a solution of potassium t-butoxide (169 g, 1.51 mol) in toluene (1.9 L) at 110° C. under $N_2$ atmosphere. The mixture was heated at reflux for 1 hour and cooled down to room temperature. Water (400 ml) was added then the layers were heated at reflux for 2 hours. After the organic layer was separated, the aqueous layer was neutralized and extracted with EtOAc for 15 hours with a continuous extraction apparatus. The combined organic layers were dried over $MgSO_4$ and concentrated. Recrystallization from ethanol gave compound 1 (34.6 g, 31%) as a colorless crystal.

TLC (silica gel): Rf=0.4 (5:1 $CH_2Cl_2$/MeOH).

(B) (3R*,4R*)-6-Benzylidene-N,N-dietyl-5-oxo-1-azabicyclo[2.2.2]octane-3carboxamide, 2

A mixture of 1 (34.6 g, 150 mmol), benzaldehyde (17.4 g, 160 mmol) and NaOH (6.5 g, 160 mmol) in 400 ml of EtOH was refluxed for 3 hours. After the reaction mixture was cooled down to room temperature, the resulting yellow crystal was collected by filtration and washed with cold EtOH and dried in vacuo to give (3R*,4R*)-6-benzylidene-N,N-diethyl-5-oxo-1-azabicyclo[2.2.2]octane-3-carboxamide 2 (38.4 g, 128 mmol). The filtrate was concentrated under reduced pressure to give a second crop (3.3 g, 11 mmol) (total 41.7 g, 139 mmol, 93%).

TLC (silica gel): Rf=0.43 (2:1 EtOAc/Hexane).

(C) (3R*,4R*)-N,N-Diethyl-6-diphenylmethyl-5-oxo-1-azabicyclo[2.2.2]-octane-3-carboxamide, 3

A 1 L 4 necked flask, equipped with a mechanical stirrer and a thermometer was flame dried and furnished with a $N_2$ atmosphere. CuBr·SMe$_2$ (3.1 g, 15 mmol) was placed in this flask, dry THF (400 ml) was added and cooled down to −50° C. To this suspension was added 3M phenylmagnesium bromide (an ether solution, 50 ml, 150 mmol) dropwise over a period 20 minutes and stirred for 30 minutes at −60° C. A solution of compound 2 (45 g, 150 mmol) dissolved in warm dry THF (100 ml) was added dropwise into this reaction suspension under a $N_2$ atmosphere over a period 1 hour. The reaction mixture was stirred at 0° C. for 1.5 hours, and saturated NH$_4$Cl aqueous (100 ml) was added to the reaction mixture and the organic layer was washed with saturated NH$_4$Cl aqueous until the blue color disappeared. The blue water layers were extracted with EtOAc (2×100 ml). The combined organic layers were washed with brine, and dried over MgSO$_4$. After filtration and evaporation of the solvent, the crude solid was purified by silica gel chromatography (Hexane:EtOAc=1:1–1:2 as an eluent) to give 1,2-adduct (1.2 g, 2%) and 1,4-adduct (compound 3, 54 g, 92%).

TLC (silica gel): 1,4-adduct (3) Rf=0.3 and 1,2-adduct Rf=0.85 (2:1 EtOAc/Hexane).

(D) (3R*,4R*)-N,N-Diethyl-6-diphenylmethyl-5,5-ethylenedioxy-1-azabicyclo[2.2.2]octane-3-carboxamide, 4

A mixture of compound 3 (10 g, 26 mmol), 1,2-bis(trimethylsiloxy)ethane (6 g, 29 mmol), trimethylsilylchloride (20 ml) and ethylene glycol (50 ml) was heated at 100° C. for 20 hours and at reflux for 3 hours. After by-products were removed by distillation (93° C./atmosphere pressure), the mixture was poured into cold NaHCO$_3$ aqueous (250 ml) and extracted with CH$_2$Cl$_2$ (100 ml) three times. The combined extracts were dried over Na$_2$SO$_4$ and concentrated. The crude was purified by recrystallization from AcOEt-hexane to give compound 4 (1:2 mixture at 6-position; 10 g, 23 mmol, 88%)

$^1$H NMR (CDCl$_3$): 4.54 (d, J=12.1 Hz; Ph$_2$CHCH of one isomer), 4.33, 4.28 (d+d, J=12 Hz; a pair of Ph$_2$CHCH and Ph$_2$CHCH of another isomer)

MS (DI-EI); M/z=434 (M+)

(E) (3R*,4S*)-N,N-Diethyl-6-diphenylmethyl-5,5-ethylenedioxy-1-azabicyclo[2.2.2]octane-3-carboxamide, 5

A suspension of compound 4 (9.8 g, 22 mmol) in sodium methoxide (28% in MeOH; 400 g) was heated at reflux for 9 hours. The resulting solution was poured on ice (300 ml) and extracted with CH$_2$Cl$_2$ (150 ml) three times. The combined extracts were dried over Na$_2$SO$_4$ and concentrated. The crude was purified by recrystallization from EtOH to give compound 5 (1:4 mixture at 6-position; 8.4 g, 19 mmol, 87%).

$^1$H NMR (CDCl$_3$): 4.40 (d, J=12.1 Hz; Ph$_2$CHCH of one isomer), 4.34, 3.93 (d+d, J=12.5 Hz; a pair of Ph$_2$CHCH and Ph$_2$CHCH of another isomer).

MS (DI-EI); M/z=434 (M+).

(F) (3R*,4S*)-6-Diphenylmethyl-5-oxo-1-azabicyclo[2.2.2]octane-3-carboxylic acid hydrochloride, 6

A solution of compound 5 (5.2 g, 12 mmol) in concentrated HCl (150 ml) was heated at reflux for 18 hours. The resulting precipitate was collected and dried to give compound 6 (1.7 g, 4.6 mmol, 38%; compound 6:(3R*,4R*)-isomer=4:1).

$^1$H NMR (CDCl$_3$): 5.70, 4.81 (d+d, J=11 Hz; a pair of Ph$_2$CHCH and Ph$_2$CHCH).

(G) (3R*,4S*)-N-Carbamoylmethyl-6-diphenylmethyl-5-oxo-1-azabicyclo[2.2.2]octane-3-carboxamide, 7

A suspension of compound 6 (one isomer; 0.93 g, 2.5 mmol) and glycinamide hydrochloride (0.34 g, 3.0 mmol) in DMF (10 ml) was treated with triethylamine (0.50 g, 5.0 mmol) at room temperature. To this suspension was added diethyl cyano phosphonate (0.46 g, 2.8 mmol) followed by triethylamine (0.28 g, 2.8 mmol) at room temperature. The mixture was stirred at room temperature for 15 hours, poured into NaHCO$_3$ aqueous (50 ml) and extracted with AcOEt three times. The combined extracts were dried over Na$_2$SO$_4$ and concentrated to give compound 7 (0.80 g, 2.0 mmol, 82%).

$^1$H NMR (CDCl$_3$): 4.48 (d, J=12 Hz; Ph$_2$CHCH of one isomer), 4.41 (d, J=12 Hz; Ph$_2$CHCH of the other isomer).

(H) (3R*,4S*,5S*,6S*)-N-Carbamoylmethyl-5-(5-isopropyl-2-methoxybenzylamino)-6-diphenylmethyl-1-azabicyclo[2.2.2]octane-3-carboxamide dihydrochloride, 8

A mixture of compound 7 (0.80 g, 2.0 mmol), 5-isopropyl-2-methoxybenzylamine (0.43 g, 2.4 mmol) and CSA (75 mg) in toluene (20 ml) was heated at reflux with removal of water for 15 hours and then the solvent was removed. The residue was dissolved in small amount of THF (2 ml) and this solution was added to a solution of sodium NaBH(AcO)$_3$ (1.3 g, 6 mmol) in acetic acid (10 ml) at room temperature. The mixture was stirred at room temperature for 15 hours and the solvent was removed. Water (30 ml) was added and the mixture was neutralized with NaHCO$_3$ and extracted with AcOEt three times. The combined extracts were dried over Na$_2$SO$_4$ and concentrated. This mixture was purified by a column chromatography on silica gel (CH$_2$Cl$_2$:MeOH=10:1). This compound was converted to dihydrochloride salt with Hcl/MeOH. The salt was purified by recrystallization from isopropanol/isopropyl ether to give compound 8 (0.10 g, 0.16 mmol, 8%)

M.p.: 178°–183° C. IR (nujol): 3400, 3160, 3035, 2965, 1671, 1505, 1455, 1255, 709 cm$^{-1}$. $^1$H NMR (CDCl$_3$): 7.39–7.00 (m, 10H), 6.72–6.30 (m, 5H), 5.69 (br, 1H), 4.47 (d, J=12 Hz, 1H), 3.93 (br, 2H), 3.55 (s, 3H), 3.88–3.51 (m, 2H), 3.21–2.42 (m, 8H), 2.39 (br, 1H), 1.90–1.50 (m, 2H), 1.24–1.13 (m, 6H).

Example 2

(3R*,4S*,5S*,6S*)-N-Carboxymethyl-5-(5-isopropyl-2-methoxybenzylamino)-6-diphenylmethyl-1-azabicyclo[2.2.2]octane-3-carboxamide hydrochloride, 9

A solution of compound 8 (free base; 0.20 g, 0.36 mmol) in concentrated HCl (5 ml) was heated at reflux for 18 hours. The resulting precipitate was collected and dried to give compound 9 (0.15 g, 0.22 mmol, 60%).

M.p.: 197°–200° C. IR (nujol): 2965, 1678, 1505, 1256 cm$^{-1}$. $^1$H NMR (CDCl$_3$): 7.50–7.96 (m, 10H), 6.65–6.52 (m, 3H), 4.55 (br, 2H), 3.93 (br 1H), 3.41 (s, 3H), 3.60–2.50 (m, 13H), 1.91 (br, 1H), 1.20–1.13 (m, 6H).

Example 3

(3R,4S,5S,6S)-3-(2-Carbamoylpyrrolidin-1-yl)carbonyl-5-(5-isopropyl-2-methoxybenzylamino)-6-diphenylmethyl-1-azabicyclo[2.2.2]octane dihydrochloride This compound was prepared from L-prolinamide and (3R,4S)-6-diphenylmethyl- 5-oxo-1-azabicyclo[2.2.2]octane-3-carboxylic acid hydrochloride in a similar manner for the synthesis of Example 1.

M.p.: 191°–194° C. IR (KBr): 3405, 3185, 2970, 1676, 1640, 1507, 1452, 1441, 1256, 710 cm$^{-1}$. $^1$H NMR (CDCl$_3$): 7.40–7.00 (m, 10H), 6.70–6.53 (m, 3H), 5.33 (br, 1H), 4.77–4.46 (m, 2H), 3.53 (s, 3H), 3.71–3.10 (m, 7H), 3.00–2.58 (m, 5H), 2.48–2.37 (m, 1H), 2.24–1.50 (m, 6H), 1.25–1.15 (m, 6H).

Example 4

(3R,4S,5S,6S)-N-(1-Carbamoylethyl)-5-(5-isopropyl-2-methoxybenzylamino)-6 -diphenylmethyl-1-azabicyclo[2.2.2]octane-3-carboxamide To a mixture of (3R,4S ,5S ,6S)-5-(5-isopropyl-2-methoxybenzylamino)-6 -diphenylmethyl-1-azabicyclo[2.2.2]octane-3-carboxylic acid dihydrochloride (300 mg, 0.5 mmol), alaninamide hydrobromide (100 mg, 0.6 mmol) and triethylamine (70 mg, 0.7 mmol) in DMF (2 ml) was added 1-ethyl-3-(3-dimethylaminopropyl)carbodiimide hydrochloride (160 mg, 0.8 mmol) at 0° C. The mixture was stirred at 0° C. for 30 minutes, then at room temperature for -14 hours. Water and NaHCO$_3$ were added and the mixture was extracted with CH$_2$Cl$_2$. The combined extracts were dried, concentrated and purified by a column chromatography on silica-gel (CH$_2$Cl$_2$/methanol=10:1) to give a title compound (220 mg, 0.39 mmol, 77%).

M.p.: 243°–245° C. IR (Kbr): 3385, 1644, 1501, 1449 cm$^{-1}$. $^1$H NMR (CDCl$_3$): 7.40–6.95 (m, 10H), 6.70–6.52 (m, 3H), 6.50–6.35 (m, 2H), 5.43 (br, 1H), 4.60–4.42 (m, 2H), 3.56 (s, 3H), 3.90–3.43 (m, 2H), 3.30–2.30 (m, 9H), 2.00–1.50 (m, 2H), 1.43–1.30 (m, 3H), 1.24–1.14 (m, 6H).

The compounds of the following examples (Examples 5–9) were prepared from (3R,4S,5S,6S)-5-(5-isopropyl-2-methoxybenzylamino)-6-diphenylmethyl-1-azabicyclo [2.2.2]octane-3-carboxylic acid dihydrochloride and each corresponding carboxamide derivative with a suitable coupling agent in a similar manner for the synthesis of Example 4.

Example 5

(3R,4S,5S,6S)-N-Carbamoylmethyl-5-(5-isopropyl-2-methoxybenzylamino)-6 -diphenylmethyl-1-azabicyclo[2.2.2]octane-3-carboxamide dihydrochloride (one diastereomer which is included in Example 1)

M.p.: 177°–180° C. IR (Kbr): 3385, 3185, 2965, 1672, 1506, 1455, 1441, 1256, 710 cm$^{-1}$. $^1$H NMR (CDCl$_3$, free base): the same data as data of Example 1 (its corresponding racemic form).

Example 6

(3R,4S,5S,6S)-N-(1-Carbamoyl-3-methylbutyl)-5-(5-isopropyl-2 -methoxybenzylamino)-6-diphenylmethyl-1-azabicyclo[2.2.2]octane-3-carboxamide M.p.: 165°–169° C. IR (Kbr): 3385, 2960, 1690, 1655, 1501, 1249 cm$^{-1}$. $^1$H NMR (CDCl$_3$): 7.43–6.60 (m, 13H), 5.48 (br, 1H), 4.60–4.10 (m, 3H), 3.53 (s, 3H), 3.70–3.18 (m, 7H), 2.98–2.60 (m, 4H), 2.10–1.55 (m, 4H), 1.25–1.20 (m, 6 H), 1.00–0.92 (m, 6H).

Example 7

(3R,4S,5S,6S)-N-(2-Carbamoylethyl)-5-(5-isopropyl-2-methoxybenzylamino-6-diphenylmethyl-1-azabicyclo[2.2.2]octane-3-carboxamide dihydrochloride M.p.: 262°–264° C. IR (Kbr): 3330, 3180, 1679, 1660, 1543, 1503, 1251 cm$^{-1}$. $^1$H NMR (CDCl$_3$, free base): 7.40–7.02 (m, 10H), 6.73–6.59 (m, 3H), 6.62 (br, 1H), 5.57 (br, 1H), 4.48(d, J=12 Hz, 1H), 3.55 (s, 3H), 3.88–3.44 (m, 4H), 3.26–3.03 (m, 5H), 2.87–2.42 (m, 6H), 1.87–1.67 (m, 1H), 1.26–1.18 (m, 6H).

Example 8

(3R,4S,5S,6S)-N-(1-Carbamoyl-2-phenylethyl)-5-(5-isopropyl-2 -methoxybenzylamino)-6-diphenylmethyl-1-azabicyclo[2.2.2]octane-3-carboxamide dihydrochloride M.p.: 203°–208° C. IR (Kbr): 3385, 3320, 3185, 2970, 1676, 1667, 1505, 1455, 1256, 709 cm$^{-1}$. $^1$H NMR (CDCl$_3$, free base): 7.40–7.00 (m, 15H), 6.70–6.55 (m, 3H), 6.30 (br, 1H), 5.97 (br, 1H), 5.49 (br, 1H), 4.75–4.44 (m, 2H), 3.54 (s, 3H), 3.70–3.50 (m, 3H), 3.20–2.95 (m, 6H), 2.82–2.35 (m, 4H), 1.58–1.43 (m, 1H), 1.25–1.10 (m, 6H).

Example 9

(3R,4S,5S,6S)-N,N-bis(Cyanomethyl)-5-(5-isopropyl-2-methoxybenzylamino)-6-diphenylmethyl-1-azabicyclo[2.2.2]octane-3-carboxamide M.p.: 195°–199° C. IR (Kbr): 3430, 2965, 1676, 1500, 1250 cm$^{-1}$. $^1$H NMR (CDCl$_3$): 7.50–6.50 (m, 13H), 4.70–4.28 (m, 5H), 3.56 (s, 3H), 4.00–2.69 (m, 10H), 2.24 (br, 1H), 1.95–1.62 (m, 2H), 1.34–1.12 (m, 6H).

Following three compounds and compounds indicated in the following table can be also prepared from the corresponding carboxamides according to the synthetic procedure of Example 1, Example 2 or Example 4.

(3R*,4S*,5S*,6S*)-3-(2-Carboxypyrrolidin-1-yl)carbonyl-5-(5-isopropyl-2-methoxybenzylamino)-2-diphenylmethyl-1-azabicyclo[2.2.2]octane;

(3R*,4S*,5S*,6S*)-3-(2-Carbamoyl-4-hydroxypyrrolidin-1-yl)carbonyl-5-(5-isopropyl-2-methoxybenzylamino)-2-diphenylmethyl-1-azabicyclo[2.2.2]octane;

(3R*,4S*,5S*,6S*)-3-(2-Carboxy-4-hydroxypyrrolidin-1-yl)carbonyl-5-(5-isopropyl-2-methoxybenzylamino)-2-diphenylmethyl-1-azabicyclo[2.2.2]octane

TABLE

Generic chemical formula

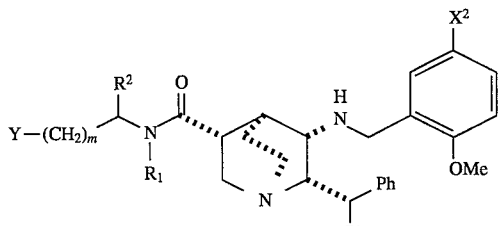

| Y | m | R² | R¹ | X² |
|---|---|---|---|---|
| H₂NCO | 0 | H | H₂NCOCH₂ | i-Pr |
| H₂NCO | 0 | H | HO₂CCH₂ | i-Pr |
| HO₂C | 0 | H | HO₂CCH₂ | i-Pr |
| HO₂C | 0 | i-Bu | H | i-Pr |
| HO₂C | 0 | Me | H | i-Pr |
| H₂NCO | 2 | HO₂C | H | i-Pr |
| HO₂C | 2 | H₂NCO | H | i-Pr |
| HO₂C | 2 | HO₂C | H | i-Pr |
| H₂NCO | 0 | H | Bn | i-Pr |
| HO₂C | 0 | H | Bn | i-Pr |
| H₂NCO | 1 | H | Bn | i-Pr |
| HO₂C | 1 | H | Bn | i-Pr |
| HO₂C | 1 | H | H | i-Pr |
| H₂NCO | 0 | H | H | OCF₃ |
| H₂NCO | 0 | H | H | SMe |
| H₂NCO | 0 | H | H | SOMe |
| H₂NCO | 0 | H | H | SO₂Me |
| H₂NCO | 0 | H | H | Et |
| H₂NCO | 0 | H | H | t-Bu |
| HO₂C | 0 | Bn | H | i-Pr |
| H₂NCO | 0 | Bn | H | i-Pr |
| HO₂C | 0 | i-Pr | H | i-Pr |
| H₂NCO | 0 | s-Bu | H | i-Pr |
| HO₂C | 0 | s-Bu | H | i-Pr |
| H₂NCO | 0 | 3-Ind-Me | H | i-Pr |
| HO₂C | 0 | 3-Ind-Me | H | i-Pr |
| H₂NCO | 0 | Bn(4-OH) | H | i-Pr |
| HO₂C | 0 | Bn(4-OH) | H | i-Pr |
| HOCH₂ | 0 | H₂NCO | H | i-Pr |
| HOCH₂ | 0 | HO₂C | H | i-Pr |
| H₂NCO | 0 | CH₃CH(OH) | H | i-Pr |
| HO₂C | 0 | CH₃CH(OH) | H | i-Pr |
| H₂NCO | 0 | CH₃S(CH₂)₂ | H | i-Pr |
| HO₂C | 0 | CH₃S(CH₂)₂ | H | i-Pr |
| H₂NCO | 0 | HSCH₂ | H | i-Pr |
| HO₂C | 0 | HSCH₂ | H | i-Pr |
| H₂NCO | 1 | H₂NCO | H | i-Pr |
| H₂NCO | 1 | HO₂C | H | i-Pr |
| HO₂C | 1 | H₂NCO | H | i-Pr |
| HO₂C | 1 | HO₂C | H | i-Pr |
| H₂NCH₂ | 3 | H₂NCO | H | i-Pr |
| H₂NCH₂ | 3 | HO₂C | H | i-Pr |
| H₂NCO | 0 | H | Me | i-Pr |
| HO₂C | 0 | H | Me | i-Pr |
| MeO₂C | 0 | H | H | i-Pr |
| EtO₂C | 0 | H | H | i-Pr |
| t-BuO₂C | 0 | H | H | i-Pr |
| BnO₂C | 0 | H | H | i-Pr |
| MeOCH₂ | 0 | H | H | i-Pr |
| HOCH₂ | 0 | H | H | i-Pr |
| H₂NCH₂ | 0 | H | H | i-Pr |
| MeHNCH₂ | 0 | H | H | i-Pr |
| Me₂NCH₂ | 0 | H | H | i-Pr |

The abbreviations in the above table mean herein as follows: i-Pr=isopropyl; i-Bu=isobutyl; s-Bu=sec-butyl; t-Bu=tert-butyl; Bn=benzyl; 3-ind-Me=3-indolylmethyl; Bn(4-OH)=4-hydroxybenzyl.

We claim:
1. A compound of the following chemical formula

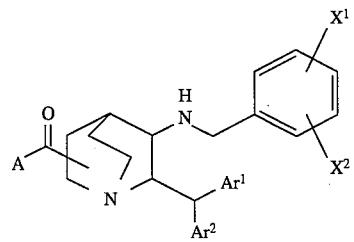

and the pharmaceutically-acceptable salts thereof, wherein $X^1$ is $C_1$–$C_5$ alkoxy or halosubstituted ($C_1$–$C_5$) alkoxy;

$X^2$ is hydrogen, halogen, $C_1$–$C_5$ alkyl, $C_2$–$C_5$ alkenyl, $C_2$–$C_5$ alkynyl, $C_1$–$C_5$ alkoxy, $C_1$–$C_5$ alkylthio, $C_1$–$C_5$ alkylsulfinyl, $C_1$–$C_5$ alkylsulfonyl, halosubstituted ($C_1$–$C_5$) alkyl, halosubstituted ($C_1$–$C_5$) alkoxy, $C_1$–$C_5$ alkylamino, dialkylamino having from 1 to 5 carbon atoms in each alkyl moiety, $C_1$–$C_5$ alkylsulfonylamino (which may be substituted by halogen), N-($C_1$–$C_5$)alkyl-N-($C_1$–$C_5$)alkylsulfonylamino (which may be substituted by halogen in the alkylsulfonyl moiety), $C_1$–$C_5$ alkanoylamino (which may be substituted by halogen) or N-($C_1$–$C_5$)alkyl-N-($C_1$–$C_5$)alkanoylamino (which may be substituted by halogen in the alkanoyl moiety);

$Ar^1$ and $Ar^2$ are each, independently, thienyl, phenyl, fluorophenyl, chlorophenyl or bromophenyl;

A is Y—$(CH_2)_m$—CH($R^2$)—$(CH_2)_n$—$NR^1$—;

$R^1$ is hydrogen, $C_1$–$C_5$ alkyl, benzyl or —$(CH_2)_p$—Y;

$R^2$ is hydrogen, $C_1$–$C_5$ alkyl (which may be substituted by the substituent which is selected from the group consisting of hydroxy, amino, methylthio and mercapto), benzyl, 4-hydroxybenzyl, 3-indolylmethyl or —$(CH_2)_p$—Y;

Y is —CN, —$CH_2Z$ or —COZ;

Z is hydroxy, amino, $C_1$–$C_5$ alkoxy, $C_1$–$C_5$ alkylamino or dialkylamino having from 1 to 5 carbon atoms in each alkyl moiety;

m, n and p are each, independently, 0, 1, 2 or 3; and $R^1$ and $R^2$ may be connected to form a ring.

2. A compound according to claim 1, wherein $X^1$ is 2-methoxy and $Ar^1$ and $Ar^2$ are each phenyl.

3. A compound according to claim 2, wherein $X^2$ is selected from the group consisting of ethyl, n-propyl, isopropyl, t-butyl, isopropenyl, methylthio, methylsulfinyl, methylsulfonyl, trifluoromethoxy, dimethylamino, N-methyl-N-methylsulfonylamino and N-methyl-N-acetylamino.

4. A compound according to claim 3, wherein Y is —CONH₂ or —COOH.

5. A compound according to claim 4, wherein $R^1$ is hydrogen.

6. A compound according to claim 5, wherein m is 0, n is 0 or 1 and $R^2$ is hydrogen, methyl, benzyl or isobutyl.

7. A compound according to claim 3, wherein $R^1$ and $R^2$ together with —CH—$(CH_2)_n$—N— form a five membered ring, n is zero, m is zero, Y is —COZ, and Z is hydroxy, amino, $C_1$–$C_5$ alkylamino or $C_1$–$C_5$ dialkylamino.

8. A compound according to claim 2, in which the configuration is (3R*,4S,5S,6S) or (2S*,4S,5S,6S).

9. A compound according to claim 1, which is selected from the group consisting of:
(3R,4S,5S,6S)-N-Carbamoylmethyl-5-(5-isopropyl-2-methoxybenzyl-amino)-6-diphenylmethyl-1-azabicyclo[2.2.2]octane-3-carboxamide;

(3R,4S,5S,6S)-N-Carboxymethyl-5-(5-isopropyl-2-methoxybenzylamino)-6-diphenylmethyl-1-azabicyclo[2.2.2]octane-3-carboxamide;

(3R,4S,5S,6S)-3-(2-Carbamoylpyrrolidin-1-yl)carbonyl-5-(5-isopropyl-2-methoxybenzylamino)-6-diphenylmethyl-1-azabicyclo[2.2.2]octane;

(3R,4S,5S,6S)-N-(1-Carbamoylethyl)-5-(5-isopropyl-2-methoxybenzylamino)-6-diphenylmethyl-1-azabicyclo[2.2.2]octane-3-carboxamide;

(3R,4S,5S,6S)-N-(1-Carbamoyl-3-methylbutyl)-5-(5-isopropyl-2-methoxybenzylamino)-6-diphenylmethyl-1-azabicyclo[2.2.2]octane-3-carboxamide;

(3R,4S,5S,6S)-N-(2-Carbamoylethyl)-5-(5-isopropyl-2-methoxybenzylamino)-6-diphenylmethyl-1-azabicyclo[2.2.2]octane-3-carboxamide;

(3R,4S,5S,6S)-N-(1-Carbamoyl-2-phenylethyl)-5-(5-isopropyl-2-methoxybenzylamino)-6-diphenylmethyl-1-azabicyclo[2.2.2]octane-3-carboxamide;

(3R,4S,5S,6S)-N,N-bis(Cyanomethyl)-5-(5-isopropyl-2-methoxybenzylamino)-6-diphenylmethyl-1-azabicyclo[2.2.2]octane-3-carboxamide;

(3R,4S,5S,6S)-N-carbamoylmethyl-5-(5-t-butyl-2-methoxybenzylamino)-6-diphenylmethyl-1-azabicyclo[2.2.2]octane-3-carboxamide;

(3R,4S,5S,6S)-N-carbamoylmethyl-5-(5-ethyl-2-methoxybenzylamino)-6-diphenylmethyl-1-azabicyclo[2.2.2]octane-3-carboxamide;

(3R,4S,5S,6S)-N-carbamoylmethyl-5-(2-methoxy-5-methylsulfonylbenzylamino)-6-diphenylmethyl-1-azabicyclo[2.2.2]octane-3-carboxamide;

(3R,4S,5S,6S)-N-carbamoylmethyl-5-(2-methoxy-5-methylsulfinylbenzylamino)-6-diphenylmethyl-1-azabicyclo[2.2.2]octane-3-carboxamide;

(3R,4S,5S,6S)-N-carbamoylmethyl-5-(2-methoxy-5-methylthiobenzylamino)-6-diphenylmethyl-1-azabicyclo[2.2.2]octane-3-carboxamide; and (3R,4S,5S,6S)-N-carbamoylmethyl-5-(2-methoxy-5-trifluoromethoxybenzylamino)-6-diphenylmethyl-1-azabicyclo[2.2.2]octane-3-carboxamide.

10. A compound according to claim 9, which is (3R,4S,5S,6S)-N-Carbamoylmethyl-5-(5-isopropyl-2-methoxybenzylamino)-6-diphenylmethyl-1-azabicyclo[2.2.2]octane-3-carboxamide.

11. A substance P antagonist which comprises a therapeutically effective amount of a compound of claim 1 or its pharmaceutically acceptable salt together with a pharmaceutically acceptable carrier.

12. A method of antagonizing substance P in a mammalian subject in need of such treatment which comprises administering to said mammalian subject an effective amount of a compound according to claim 1.

13. A pharmaceutical composition for the treatment of gastrointestinal disorders, central nervous system disorders, inflammatory diseases, asthma, pain or migraine which comprises a therapeutically effective amount of a compound of claim 1 or its pharmaceutically acceptable salt together with a pharmaceutically acceptable carrier.

14. A method of treating gastrointestinal disorders, central nervous system disorders, inflammatory diseases, asthma, pain or migraine in a mammalian subject in need of such treatment which comprises administering to said mammalian subject an effective amount of a compound according to claim 1.

* * * * *